(12) United States Patent
Lamas et al.

(10) Patent No.: US 6,648,017 B2
(45) Date of Patent: Nov. 18, 2003

(54) VALVE ARRANGEMENT FOR A MEDICAL APPARATUS

(75) Inventors: Gustavo Lamas, Onex (CH); Lutz Beerstecher, Borex (CH)

(73) Assignee: Ferton Holding S.A. (CH)

( * ) Notice: Subject to any disclaimer, the term of this patent is extended or adjusted under 35 U.S.C. 154(b) by 83 days.

(21) Appl. No.: 10/104,637

(22) Filed: Mar. 21, 2002

(65) Prior Publication Data

US 2002/0162590 A1 Nov. 7, 2002

(30) Foreign Application Priority Data

Mar. 23, 2001 (DE) .......................................... 101 14 330

(51) Int. Cl.⁷ .............................................. F16K 11/16
(52) U.S. Cl. ...................... 137/595; 137/601.12; 251/7; 604/250
(58) Field of Search ................................ 137/595, 597, 137/601.12; 251/7, 251; 604/250

(56) References Cited

U.S. PATENT DOCUMENTS 3,550,619 A * 12/1970 Halasz ....................... 137/595
4,017,974 A   4/1977 Sotman et al. .................. 32/28
4,194,535 A * 3/1980 Galland et al. ........ 137/601.01
5,117,870 A * 6/1992 Goodale et al. ............... 251/7

FOREIGN PATENT DOCUMENTS

DE        692819        6/1940
EP      0 422 855       4/1991

* cited by examiner

Primary Examiner—Stephen M. Hepperle
(74) Attorney, Agent, or Firm—Ostrolenk, Faber, Gerb & Soffen, LLP

(57) ABSTRACT

A valve arrangement for stopping fluid passage through at least one flexible tubing is provided with a camshaft having at least one control cam which is designed as a sink in an otherwise closed circular surface of the camshaft for moving a press member which is retracted into an inactive relative position when radially aligned with the sink and which is protruded into an active relative position by the circular surface of the camshaft for then squeezing the associated portion of the flexible tube which is passed through a housing of the valve arrangement in a direction normal with respect to a longitudinal bore rotatably supporting the camshaft and also normal with respect to a radial bore which is arranged for radially guiding the press member.

10 Claims, 2 Drawing Sheets

VALVE ARRANGEMENT FOR A MEDICAL APPARATUS

FIELD OF THE INVENTION

The present invention relates to a valve arrangement for a medical apparatus for stopping fluid passage through a flexible tubing.

BACKGROUND OF THE INVENTION

A prior art valve arrangement for a medical apparatus of the kind as herein referred is described in U.S. Pat. No. 4,960,259. This known valve arrangement is intended for being used with an infusion device and comprises a stepped bore into a larger diameter of which a portion of a flexible tubing is inserted. An infusion cannula is arranged for being axially projected from one end of the stepped bore having the larger diameter to its opposite end having the smaller diameter for being inserted into a catheter tube which is taken up by this smaller diameter of the stepped bore. For allowing a fluid passage through the associated portion of the flexible tubing which is axially aligned with the associated end of the catheter tube and the associated end of the infusion cannula the flexible tubing must first be released from a radially directed pressure of a press member which in a protruded active relative position normally squeezes the flexible tubing at an intermediate position for stopping fluid passage through the flexible tubing. The press member is guided by a radial bore of a radially extending neck portion of a valve housing incorporating the stepped bore and may be moved by means of a screw connection into a retracted inactive relative position in which pressure is released from the flexible tubing and therefore fluid passage through the infusion cannula when inserted into the catheter tube will be allowed.

German Patent DE 690 07 003 T2 discloses a valve arrangement which is intended for being used with a linear peristalsis pump. A flexible tubing is connected with a fluid reservoir and is passed through a housing for being alternately squeezed in a first position and in a second position by a series of pump fingers for obtaining a displacement of the fluid which is captured in the flexible tubing when the pump fingers are alternately retracted into an inactive relative position for releasing their pressure on the flexible tubing. The pump fingers are moved by a corresponding number of control curves of a camshaft which is rotateably supported in a longitudinal bore of the housing. The longitudinal bore extends parallel to the portion of the flexible tubing which is passed through the housing. The pump fingers will therefore be moved by the associated control curves of the camshaft between a protruded active relative position for squeezing the flexible tube and a retracted inactive relative position for allowing a delivery of the fluid through the associated portion of the flexible tubing.

SUMMARY OF THE INVENTION

An object of the present invention is to provide a valve arrangement of the kind as above referred which may be enlarged in a simple manner for also allowing a control of a fluid passage through at least a second flexible tubing which is connected with the same or with a different medical apparatus for being alternately supplied with the same fluid or with different fluids.

The present invention accordingly provides a valve arrangement for a medical apparatus for stopping fluid passage through a flexible tubing which is characterised by the features as outlined in the claims.

A valve arrangement in accordance with the present invention therefore provides a rather simple measure for allowing an enlargement by the provision that the flexible tubing is passed through the valve housing in a direction normal with respect to the longitudinal bore rotatably supporting the camshaft and also normal with respect to the moving direction of the press member. With the provision of at least a second press member at an axially offset position of the camshaft fluid passage through at least a second flexible tubing which will be arranged side-by-side with a first flexible tubing may therefore be controlled by an associated second control cam of the camshaft. Such a multiple control of a fluid passage through multiple flexible tubings is further simplified by a design of each control cam as a sink of the otherwise circular surface of the camshaft so that when an associated press member radially aligned with such a sink the same will determine a retracted inactive relative position of the press member for allowing fluid passage through the associated portion of a flexible tubing. The press member will on the other hand be moved into a protruded active relative position by the closed circular surface of the camshaft for then squeezing the associated portion of a flexible tubing and for stopping fluid passage.

Other objects, features and advantages of the present invention will become apparent from reading the following description of a preferred embodiment of a valve arrangement according to the present invention.

DETAILED DESCRIPTION

Figure 1:
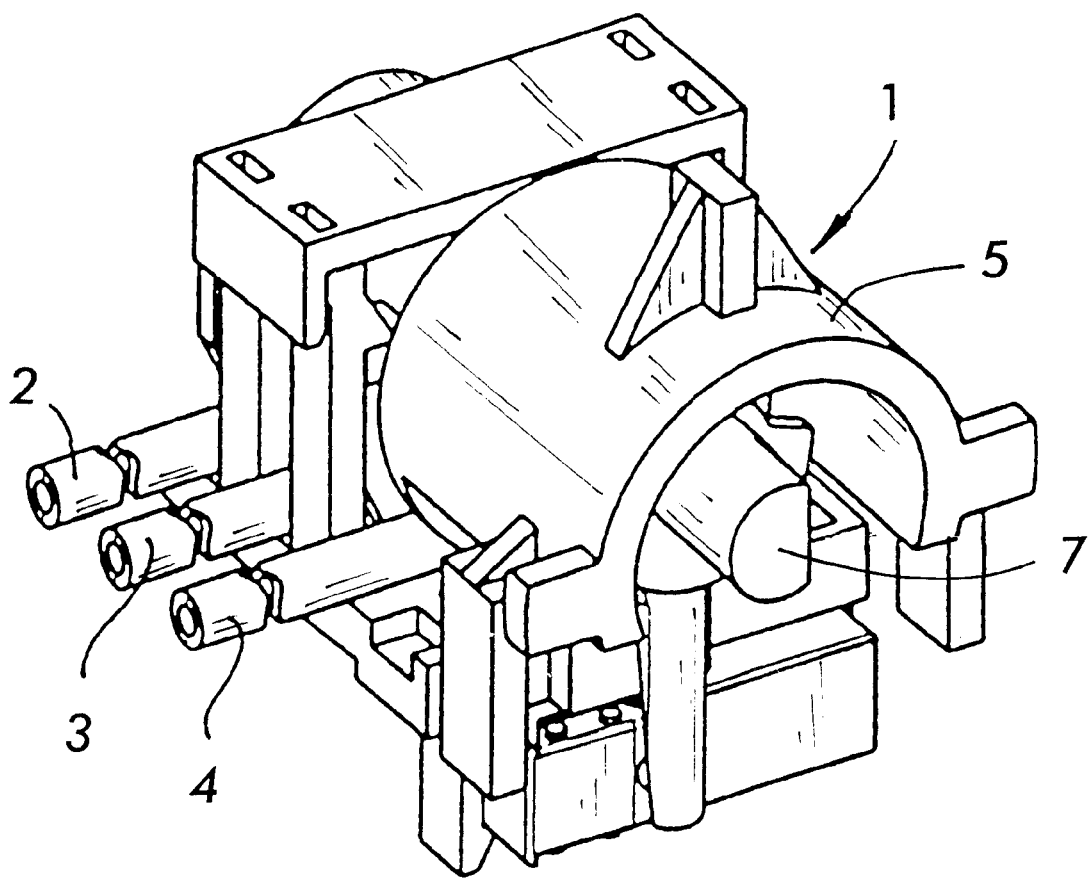
FIG. 1 is a perspective view of a valve arrangement according to the present invention.

The valve arrangement illustrated in the drawing is intended for being used with a dental apparatus which has an interconnected handpiece for dental treatment. The handpiece is intended for being selectively supplied with two different fluids which are contained in two separate fluid reservoirs of the dental apparatus comprising two associated flexible tubings whereby measure is further provided for allowing a supply of fresh water through an associated third flexible tube of the handpiece. A selective supply of the two different fluids shall be controlled by the illustrated valve arrangement in a switch-on position of an associated suction pump which on the other hand should be switched-off when the handpiece is supplied with fresh water.

In accordance with such a concept of a fluid control a valve arrangement 1 according to the present invention is associated with three flexible tubings 2, 3 and 4 which connect to a handpiece of a dental apparatus for being selectively supplied with different fluids. The three flexible tubings are passed side-by-side through a housing 5 of the valve arrangement whereby the length of the respective portion of a flexible tubing which is passed through the housing determines the design width of the valve arrangement.

The valve housing 5 comprises a longitudinal bore 6 which is realised as a stepped bore and provided for supporting rotatably a camshaft 7. The camshaft 7 has a closed circular surface 7' which is provided with axially offset sinks such as a sink 8 at those locations where the portions of the flexible tubings 2, 3 an 4 are passed through the valve housing. Press members 9, 10 and 11 at the same locations may therefore be retracted into an inactive relative position when radially aligned with an associated sink of the camshaft. The mutual distance between axially successive sinks in the surface of the camshaft 7 corresponds on the other hand with radial bores 12, 13 an 14 by which the press members 9, 10 and 11 are guided in a radial direction for their contact with an associated portion of a flexible tubing which is passed through a free space 15 which is openly connected with the longitudinal bore 6 via these radial bores.

Figure 3:
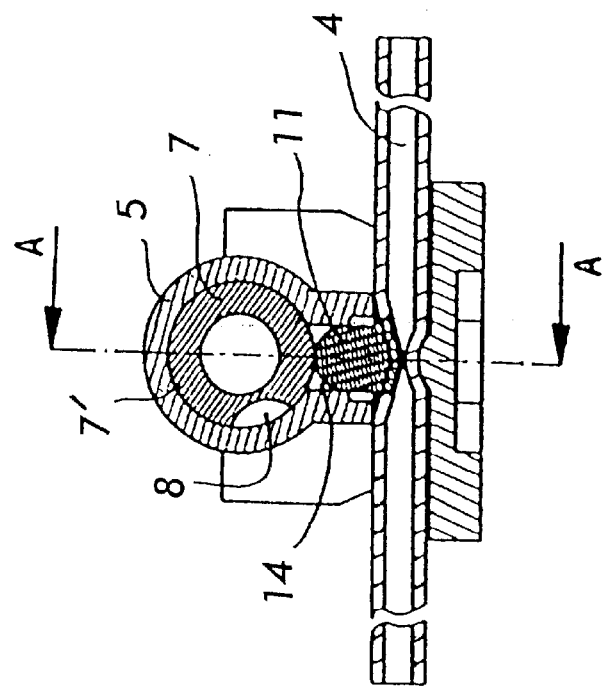
FIG. 3 is a cross section of the valve arrangement along a section line C—C in FIG. 2.
Figure 2:
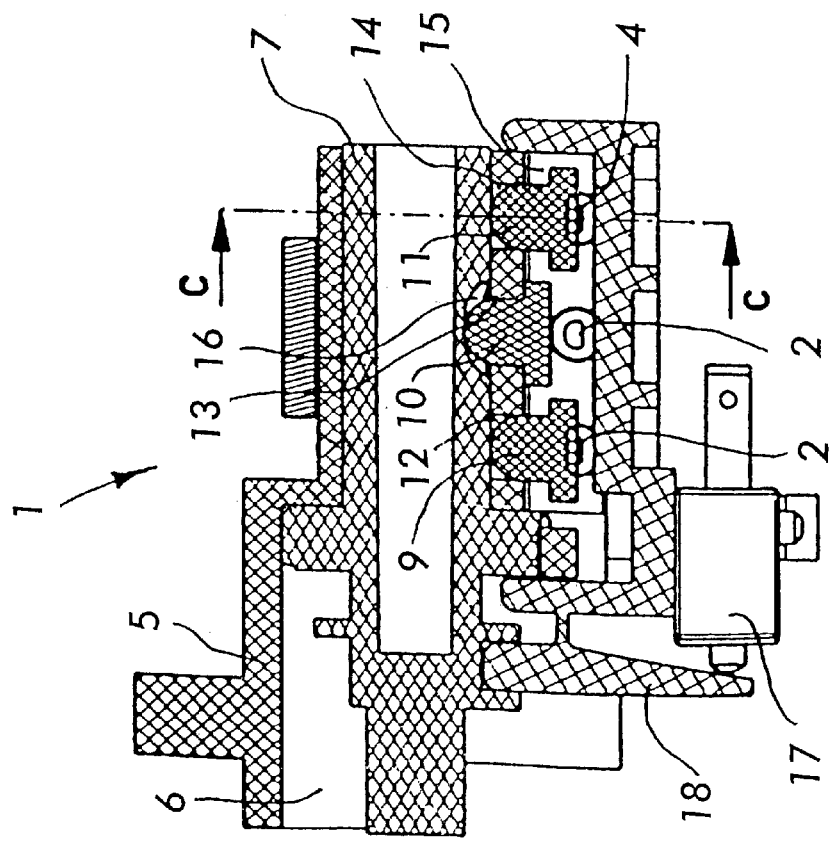
FIG. 2 is a longitudinal section of the valve arrangement along a section line A—A in FIG. 3.

The sinks of the camshaft 7 such as the sink 8 are provided at axially offset positions of the otherwise closed circular surface 7' of the camshaft 7 at circumferential positions of a mutually different central angle. With these sinks different movement sequences will be obtained for the press members 9, 10 and 11 with respect to a squeezing and a releasing of an associated portion of the flexible tubings 2, 3 and 4. As may be derived from the illustrations in FIGS. 2 and 3 it should therefore be noted that when for example the press member 11 at the location of the flexible tubing 4 is in contact with the closed circular surface 7' of the camshaft 7 it will then be pressed into a protruded active relative position for squeezing the associated portion of the flexible tube and therefore stopping a fluid passage through this portion. Press member 10 will then be radially aligned with its associated sink 16 and will therefore be retracted into its inactive relative position in which the associated portion of the flexible tubing 3 will not be squeezed and fluid passage will be allowed. Press member 9 at the location of the flexible tubing 2 will then be protruded into its active relative position also by the closed circular surface 7' of the camshaft 7 so that fluid passage through the flexible tubing 2 will then as well be stopped.

By turning the camshaft 7 it will then become possible that for example the sink 8 is radially aligned with the press member 11 so that the same will then be retracted into its inactive relative position. This retraction of the press member 11 will be supported by the pressure of the fluid which will then be allowed to pass through the flexible tubing 4 and which will therefore expand the wall of the flexible tubing. At the same time the two other sinks in the surface of the camshaft 7 will be rotated into angular positions in which the press member 9 will continuously remain in contact with the closed circular surface 7 of the camshaft for continuously squeezing the associated portion of the flexible tubing 2 whereas the press member 10 will then also be protruded into its active relative position for stopping a fluid passage through the associated portion of the flexible tubing 3.

A turning of the camshaft 7 could be effected manually by means of a handle or alternatively by an electric step motor which will be installed in the housing of the dental apparatus. The valve arrangement could also comprise a microswitch 17 for switching on and off a suction pump which would be provided for a supply of the fluids through the different flexible tubings whereby this microswitch would be actuated by a switch lever 18 that is arranged on the valve housing 5 and operatively coupled with the camshaft. A suction line of the suction pump being connected with two flexible tubings upstream of the valve arrangement would be connected downstream of the valve arrangement with a common connecting line of an associated dental handpiece.

The camshaft 7 could further be arranged for being turned into a first neutral control position in which all press members would be protruded into their active relative position so that the associated portions of the three flexible tubings will be squeezed for stopping fluid passage. This first neutral control position could alternatively also be provided only for a selection under the individual press members. There could further be provided a second neutral control position by a turning of the camshaft in which the microswitch would be actuated for switching off the associated suction pump as long as fresh water will be supplied to the handpiece through an associated supply line.

It should be further understood that the individual sinks could also be used for a mass flow control of the fluid passing through an associated portion of a flexible tubing. Any sink which would be arranged for allowing a mass flow control would then be less shallow than a sink by which the fluid passage through a flexible tubing is controlled. It should of course also be understood that the control activities of the valve arrangement according to the present invention may be simply enlarged by further extending the length of the camshaft in combination with an enlarged design width of the valve housing and a corresponding multiple arrangement of individual control cams for moving a corresponding multiple number of press members relative to a corresponding number of flexible tubings. The design of the press members will not be limited to the illustration shown in the drawing. Additional compression springs could be further used for retracting the press members into their inactive relative position.

We claim:

1. A valve arrangement for a medical apparatus for stopping fluid passage through a flexible tubing, comprising:

a valve housing through which a portion of the flexible tubing is passed, a camshaft which is rotatably supported in a longitudinal bore of the valve housing and which has at least one control cam for moving and guiding at least one press member in a first radial bore which extends in a radial direction with respect to a longitudinal bore, the press member being moved between a retracted inactive relative position and a protruded active relative position in which the associated portion of the flexible tubing is squeezed by the press member for stopping fluid passage through the flexible tubing;

said portion of the flexible tubing passing through the valve housing extends in a direction normal with respect to the longitudinal bore rotatably supporting the camshaft and also normal with respect to the radial bore which is arranged for guiding said at least one press member, said at least one control cam is formed by a first sink of the otherwise closed circular surface of the camshaft which when being radially aligned with said at least one press member determines a retracted inactive relative position of the press member the corresponding protruded active relative position of which is obtained with the closed circular surface of the camshaft which is contacted by the press member while the camshaft is rotated.

2. The valve arrangement according to claim 1, wherein the camshaft has at least a second control cam for moving and guiding at least a second press member in a second radial bore of the valve housing at a position in which a portion of at least a second flexible tubing is passed through the valve housing, said at least second control cam being formed by a second sink which is axially offset from said first sink on the otherwise closed circular surface of the camshaft at a circumferential position of a different central angle than said first sink.

3. The valve arrangement according to claim 2, wherein said first and second sinks which are axially and circumferentially offset with respect to each other determine the timing for stopping fluid passage through the one flexible tubing and the at least second flexible tubing alternately by said at least one and second press members in their protruded active relative position for squeezing an adjacent portion of a flexible tubing in two different turning positions of the camshaft.

4. The valve arrangement according to claim 3, wherein the one and the at least second flexible tubings are connected downstream of the valve arrangement with a common connecting line by which the fluids which are carried by these flexible tubings upstream of the valve arrangement are alternately supplied to an interconnected medical apparatus.

5. The valve arrangement according to claim 1, wherein the camshaft may be turned into a first neutral control position in which said at least one press member is arranged in its protruded active relative position.

6. The valve arrangement according to claim 1, wherein the camshaft may be turned into a second neutral control position in which a microswitch is actuated by a switch lever that is operatively coupled with the camshaft for switching on and off a pump which is provided for feeding the fluid.

7. The valve arrangement according to claim 1, wherein the camshaft may be manually turned by a turning handle which is provided on a medical apparatus in which the valve arrangement is housed.

8. The valve arrangement according to claim 1, wherein the camshaft may be turned by a step motor.

9. The valve arrangement according to claim 1, wherein at least a further control cam of the camshaft is arranged for allowing a mass flow control of the fluid passing through an associated portion of a flexible tubing.

10. The valve arrangement according to claim 9, wherein a sink forming the further control cam of the camshaft for allowing a mass flow control of the fluid is less shallow than a sink by which fluid passage through a flexible tubing is controlled.

* * * * *